United States Patent [19]

Yamada et al.

[11] 4,349,546
[45] Sep. 14, 1982

[54] D-ALLOSE DERIVATIVE AND PREPARATION METHOD THEREFOR

[75] Inventors: Masahide Yamada, Yokohama; Kenichi Edanami, Kamakura; Toshio Kuroda, Sagamihara, all of Japan

[73] Assignee: Wakamoto Pharmaceutical Co., Ltd., Nihonbashimuro, Japan

[21] Appl. No.: 245,920

[22] Filed: Mar. 20, 1981

[30] Foreign Application Priority Data

Mar. 24, 1980 [JP] Japan ................................. 55-36200

[51] Int. Cl.³ ...................... A61K 31/70; C08B 37/00
[52] U.S. Cl. ..................................... 424/180; 536/53
[58] Field of Search .......................... 424/180; 536/53

[56] References Cited

U.S. PATENT DOCUMENTS 4,156,777  5/1979  Kimura ................................. 536/53
4,211,866  7/1980  Matsumura ......................... 536/53
4,241,052 12/1980  Tsujihara ............................. 536/53

Primary Examiner—Alan Siegel
Attorney, Agent, or Firm—Bucknam and Archer

[57] ABSTRACT

3-[3-(2-Haloethyl)-3-nitrosoureido]-3-deoxy-D-alloses are new, antitumor compounds having a far lower myelotoxicity as compared with conventional antitumor agents. They are obtained by treating 3-[3-(2-haloethyl)ureido]-3-deoxy-1,2,5,6,-di-O-isopropylidene-α-D-allofuranoses with a nitrosating agent and then hydrolyzing the protective group in the presence of an acid.

4 Claims, No Drawings

D-ALLOSE DERIVATIVE AND PREPARATION METHOD THEREFOR

BACKGROUND OF THE INVENTION

The present invention relates to new D-allose derivatives, and more particularly, to new D-allose type nitrosourea derivatives and a process for the preparation thereof as well as a new antitumor agent containing the derivative as an active ingredient.

Various nitrosourea derivatives have been synthesized by many researchers and it has been reported that these derivatives exhibit antitumor effects.

It is known that nitrosourea derivatives, such as 1-(2-chloroethyl)-2-(methylcyclohexyl)-1-nitrosourea (Me-CCNU), 1,3-bis-(2-chloroethyl)-1-nitrosourea (BCNU) and 1-(2-chloroethyl)-3-cyclohexyl-1-nitrosourea (CCNU), are effective against early stage encephalophyma, melanoma, lymphoma, etc.

Further, various compounds, such as streptozotocin (J. Amer. Chem. Soc., 89, 4808 (1967)), chlorozotocin (J. Med. Chem., 18 (1), 104 (1975)) and glycopyranoside amine derivatives (Jap. Pat. Laid-Open No. 144319/1979), are known as sugar nitrosourea derivatives, and it has been reported that they exhibit antitumor effects.

However, in order for a certain compound to be effective as an excellent antitumor agent, the compound should act specifically and selectively on tumor cells with a minimal effect on normal cells.

The inventors have perfected the present invention upon conducting intensive investigations made for the purpose of obtaining compounds which are extremely safe and which exhibit excellent antitumor effects.

SUMMARY OF THE INVENTION:

An object of the present invention is to provide new D-allose derivatives.

Another object of the present invention is to provide a process for preparing the allose derivatives.

Still another object of the present invention is to provide an antitumor agent which contains the above allose derivative as an active ingredient, and which is safer than conventional antitumor agents.

The present invention relates to new D-allose derivatives of the formula:

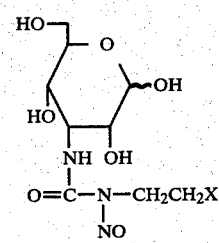

wherein X represents a halogen atom.

DETAILED DESCRIPTION OF THE INVENTION:

The derivatives of the present invention are new and are safer than conventional antitumor agents, and they are particularly effective against leukemia, Lewis lung carcinoma, melanoma, etc.

New D-allose derivatives (1) of the present invention, i.e., 3-[3-(2-haloethyl)-3-nitrosoureido]-3-deoxy-D-alloses, can be prepared by treating compounds of the formula:

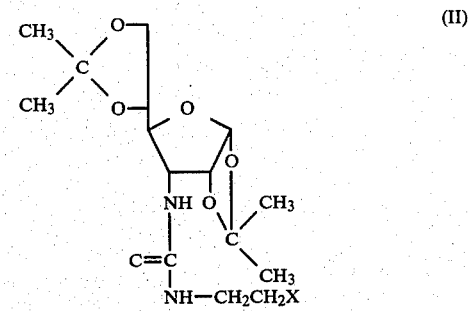

wherein X represents a halogen atom, with a nitrosating agent and then hydrolyzing the protective group in the presence of a suitable acid.

Nitrosating agents which may be used in the process of the present invention are alkali metal nitrites such as sodium nitrite and potassium nitrite; nitrous acid lower esters such as amyl nitrite and butyl nitrite; dinitrogen trioxide; and nitrogen tetroxide. Among them, sodium nitrite and potassium nitrite are preferred.

The nitrosating agent is used in an amount of 1 to 5 moles, preferably 1.1 to 1.5 moles, per mole of the starting compound (II).

Acids which may be used in the present invention are inorganic acids and organic acids, for example, trifluoroacetic acid, acetic acid, formic acid and hydrochloric acid. Among them, trifluoroacetic acid is preferred.

The reaction is carried out preferably at a pH of 1 to 3. However, if an inorganic acid is used, it is preferred to carry out the reaction in a two-phase system of ether-water or chloroform-water.

The reaction temperature is 0° to 5° C., preferably approximately 2° C.

The reaction time and pressure are not particularly critical. The reaction is effected generally for ½ to 1 hour under atmospheric pressure.

The resulting product is then concentrated by suitable known means at 20° to 40° C., preferably 25° to 30° C., and thereafter subjected to a desalting treatment with an ion exchange resin such as a strongly acidic resin, e.g. Amberlite IR 120 (H+).

The purification is effected by, for example, silica gel (WAKO C-300) chromatography in an ordinary manner.

Starting compounds (II) are also new. They can advantageously be prepared as follows:

3-Amino-3-deoxy-1,2,5,6-di-O-isopropylidene-α-D-allofuranose (see Carbohydr. Rev., 6, 276 (1968)), used as starting material, is treated with a corresponding urea-forming agent such as chloroethyl isocyanate, bromoethyl isocyanate or iodoethyl isocyanate to form compound (II).

The resulting new D-allose derivatives (I) of the present invention have $LD_{50}$ for mice of 65.5 to 550 mg/kg as will be shown by the results of the animal tests given below. D-allose derivatives (I) are highly safe antitumor agents having a far lower myelotoxicity than 1-(2-chloroethyl)-2-(4-methylcyclohexyl)-1-nitrosourea (Me-CCNU) used ordinarily.

The antitumor agents of the present invention can be administered in various ways such as by peroral administration, intraperitoneal administration and intravenous administration.

They can be used as they are or in the form of a mixture with a pharmaceutically allowable, known excipient, another auxiliary, etc. in various forms such as tablets, pills, granules, powders, capsules, syrups and injections.

In particular, when the antitumor agent is used as an injection, water having a low toxicity to the living body is preferably employed as a diluent, since administration is accomplished by direct injection into the body. The antitumor agent of the present invention fully satisfies this requirement, since it is soluble in water.

The antitumor agent of the present invention can be used along with another antitumor agent or carcinostatic agent, an antibiotic, an antiinflammatory agent or an immunity activator.

Excipients which may be used are, for example, polyvinylpyrrolidone, sodium chondroitin sulfate, gelatin, human serum albumin, dextran T-10, calcium gluconate, calcium pantothenate, calcium lactate, $\beta$-cyclodextrin, lactose, starch, magnesium stearate, talc, vegetable oils, carboxymethyl cellulose, propylene glycol, hydroxypropyl cellulose, citric acid, sodium primary phosphate, mannitol and polyvinyl alcohol.

The following examples further illustrate the present invention but by no means limit its scope.

EXAMPLE 1

2.0 g of 3-[3-(2-chloroethyl)ureido]-3-deoxy-1,2,5,6-di-O-isopropylidene-$\alpha$-D-allofuranose was dissolved in 20 ml. of 85% trifluoroacetic acid and the solution was cooled to from 0° to 5° C. Then, 0.5 g of sodium nitrite was added to the solution and which was then stirred for one hour and concentrated at room temperature under reduced pressure. The resulting oily residue was dissolved in a small quantity of water and the solution was passed through a column packed with Amberlite IR 120 (H+) resin. Water was then passed through the column and a fraction eluted was concentrated at a temperature of not more than 40° C. under reduced pressure. The resulting oily product was dissolved in a small quantity of methanol and adsorbed on silica gel (WAKO C-300, 0.5 g). It was then placed at the top of a silica gel column and subjected to elution with chloroform-methanol (9:1 V/V). The eluted fraction was concentrated at a temperature of not more than 40° C. under reduced pressure and then dried also under reduced pressure to obtain 0.5 g of 3-[3-(2-chloroethyl)-3-nitrosoureido]-3-deoxy-D-allose as light yellow powder. Yield: 31.3%.

Melting point: 56°–59° C. (decomp.)

$[\alpha]_D^{22}$: +20° (C=1.09 CH$_3$OH)

Elemental analysis as C$_9$H$_{16}$N$_3$O$_7$Cl: Calculated: C: 34.46%, H: 5.14%, N: 13.40%. Found: C: 34.25%, H: 5.03%, N: 13.12%

IR Spectrum (KBr)
 1680 cm$^{-1}$ ($\nu_{C=O}$)
 1500 cm$^{-1}$ ($\nu_{N=O}$)

NMR Spectrum (CH$_3$OD—TMS)
 $\delta$4.10 (2H, t, J=6 Hz, N—CH$_2$—)
 $\delta$5.10 (4/5 H, d, J$_{1,2}$=6 Hz, $\beta$—H$_1$)
 $\delta$5.27 (1/5 H, d, J$_{1,2}$=4 Hz, $\alpha$—H$_1$)
 $\delta$8.50 (1 H, d, j$_{3,NH}$=9 Hz, NH)

The following reference example concretely illustrates a process for preparing a starting compound of formula (II) used for the preparation of the compound of the present invention.

REFERENCE EXAMPLE 3.0 g of 3-amino-3-deoxy-1,2,5,6-di-O-isopropylidene-$\alpha$-D-allofuranose was dissolved in 50 ml. of anhydrous acetone and the solution was cooled to from 0° to 5° C. 2.0 ml. of 2-chloroethyl isocyanate was then added to the solution while stirring. After stirring for one hour, the mixture was concentrated under reduced pressure. The resulting oily residue was agitated together with ether. The crystals precipitated out were filtered out and recrystallized from 2-propanol to obtain 3.07 g of 3-[3-(2-chloroethyl)ureido]-3-deoxy-1,2,5,6-di-O-isopropylidene-$\alpha$-D-allofuranose. Yield: 61%.

Melting point: 157°–158.5° C.

$[\alpha]_D^{22}$: +40° (C=1, CHCl$_3$)

Elemental analysis as C$_{15}$H$_{25}$N$_2$O$_6$Cl: Calculated: C: 49.38%, H: 6.91%, N: 7.68%. Found: C: 49.51%, H: 6.98%, N: 7.49%

IR Spectrum (KBr)
 3390 cm$^{-1}$ ($\nu_{N-H}$)
 1690 cm$^{-1}$ ($\nu_{C=O}$)

NMR spectrum (CDCl$_3$—TMS)
 $\delta$1.30, 1.43, 1.50 (12H, s$\times$3, CH$_3$)
 $\delta$3.57 (4H, s, CH$_2$CH$_2$Cl)
 $\delta$4.55 (1H, t, J$_{1,2}$=J$_{2,3}$=4 Hz, H$_2$)
 $\delta$5.50 (1H, d, J=7 Hz, NH)
 $\delta$5.75 (1H, d, J$_{1,2}$=4 Hz, H$_1$)
 $\delta$5.75 (1H, NH).

The following animal tests illustrate the antitumor effects of 3-[3-(2-chloroethyl)-3-nitrosoureido]-3-deoxy-D-allose (hereinafter referred to as CNUA) which is one of the new nitrosourea derivatives of formula (I) of the present invention.

Test Example 1 Antileukemia test:

(1) Test animals: About 6-week old CDF mice each weighing 22±1 g; one group comprising 7 male mice.

(2) Test Method:

1×10$^5$ Leukemia L-1210 cells per mouse were implanted into the abdomen of each mouse. After 24 hours, a given amount of CNUA dissolved in isotonic sodium chloride solution was administered to the mice in through three different methods, i.e. intraperitoneal administration, intravenous administration and peroral administration. The rate of apothanacia (%) and number of survivals after 60 days were examined.

(3) Test results:

The test results are shown in Table 1.

TABLE 1

| Dose (mg/kg/day) | Method of[a] administration | ILS[b] (%) | Number of[c] survivals |
|---|---|---|---|
| 11.3 | ip, day 1 | 86 | 1/7 |
| 22.5 | " | 157 | 3/7 |
| 45 | " | >757 | 7/7 |
| 60 | " | >757 | 4/7 |
| 11.3 | ip, day 1–3 | 143 | 1/7 |
| 22.5 | " | >757 | 5/7 |
| 45 | " | >757 | 5/7 |
| 60 | " | >757 | 4/7 |
| 5 | iv, day 1 | 29 | 0/7 |
| 10 | " | 43 | 0/7 |
| 20 | " | 86 | 1/7 |
| 40 | " | >757 | 4/7 |
| 50 | " | 400 | 2/7 |
| 100 | po, day 1 | 86 | 0/7 |
| 200 | " | 100 | 3/7 |
| 300 | " | 100 | 2/7 |

TABLE 1-continued

| Dose (mg/kg/day) | Method of[a] administration | ILS[b] (%) | Number of[c] survivals |
|---|---|---|---|
| 400 | " | 57 | 2/7 |

[a]Symbols in the column of "Method of Administration" have the following meanings:
ip: Intraperitoneal administration,
iv: Intravenous administration,
po: Peroral administration,
day 1: A given amount of CNUA was administered once 24 hours after the implantation of L-1210.
day 1-3: Continuous administration once a day for three days subsequently to day 1.
[b]Rate of apothanasia % (ILS) was calculated according to the following equation:

$$ILS = \frac{\left(\begin{array}{c}\text{Number of average}\\ \text{survival days in}\\ \text{treated group}\end{array}\right) - \left(\begin{array}{c}\text{Number of average}\\ \text{survival days in}\\ \text{control group}\end{array}\right)}{\left(\begin{array}{c}\text{Number of average survival}\\ \text{days in treated group}\end{array}\right)} \times 100$$

[c]Number of survivals means the number of mice which survived for 60 days or longer in the group consisting of the 7 mice tested.

Test Example 2 Antileukemia test:

(1) Test animals: The same animals as in Test 1.
(2) Test method:
$1 \times 10^5$ Leukemia P-388 cells per mouse were implanted into the abdomen of each mouse. After 24 hours, a given amount of CNUA dissolved in isotonic sodium chloride solution was administered to the mice. The rate of apothanasia (%) and number of survivals after 60 days were examined.
(3) Test results:
The test results are shown in Table 2.

TABLE 2

| Dose (mg/kg/day) | ILS (%) | Number of survivals |
|---|---|---|
| 3.75 | 50 | 0/7 |
| 7.5 | 90 | 0/7 |
| 15 | 240 | 3/7 |
| 30 | >500 | 5/7 |
| 45 | >500 | 7/7 |
| 60 | >500 | 6/7 |

Test Example 3 Test of therapeutical effects on Lewis lung carcinoma:

(1) Test animals: About 6-week old BDF mice each weighing $22 \pm 1$ g; one group comprising 7 male mice.
(2) Test method:
$5 \times 10^5$ Lewis lung carcinoma cells per mouse were implanted under the skin of each mouse. After 24 hours, a given amount of CNUA was administered to the mice through method, i.e. intraperitoneal administration and peroral administration. The rate of apothanasia and number of survivals after 60 days were examined.
(3) Test results:
The test results are shown in Table 3.

TABLE 3

| Dose mg/kg/day | Method of administration* | ILS (%) | Number of survivals |
|---|---|---|---|
| 5 | ip, day 1 | 0 | 0/7 |
| 10 | " | 0 | 0/7 |
| 20 | " | 68 | 2/7 |
| 40 | " | >172 | 6/7 |
| 2.23 | ip, day 1-9 | 4 | 0/7 |
| 4.45 | " | 21 | 1/7 |
| 6.67 | " | 29 | 0/7 |
| 15 | iv, day 1 | 35 | 0/7 |
| 30 | " | 80 | 1/7 |
| 40 | " | >200 | 6/7 |

TABLE 3-continued

| Dose mg/kg/day | Method of administration* | ILS (%) | Number of survivals |
|---|---|---|---|
| 50 | " | >200 | 5/7 |

*"day 1-9" in the column of "Method of Administration" indicates continuous administration once/day for 9 days subsequently to "day 1".

Test Example 4 Test of therapeutical effects on melanoma:

(1) Test animals: Six-week old BDF mice each weighing $22 \pm 1$ g; one group comprising 7 male mice.
(2) Test method:
$5 \times 10^5$ $\beta$-16 melanoma cells per mouse were implanted under the skin of each mouse. After 24 hours, a given amount of CNUA was administered in two ways, i.e., intraperitoneal administration and peroral administration. The rate of apothanasia and number of survivals after 60 days were examined.
(3) Test Results:
The test results are shown in Table 4.

TABLE 4

| Dose mg/kg/day | Method of administration | ILS (%) | Number of survivals |
|---|---|---|---|
| 5 | day 1, ip | 0 | 0/7 |
| 10 | " | 16 | 0/7 |
| 20 | " | 48 | 1/7 |
| 40 | " | 60 | 2/7 |
| 1.12 | day 1-9, ip | 10 | 0/7 |
| 2.23 | " | 25 | 0/7 |
| 4.45 | " | 30 | 0/7 |
| 6.67 | " | 35 | 0/7 |
| 20 | day 1, iv. | 65 | 1/7 |
| 40 | " | 155 | 1/7 |
| 60 | " | 35 | 0/7 |

Test Example 5

(1) Test animals:
100 mg/kg of ethylnitrosourea was given intraperitoneally to DDY mice 3 to 4 days prior to delivery. After delivery, mice born with lung autotumor were used as the test animals. One group consisted of 10 mice.
(2) Test method:
Four weeks after birth, a given amount of CNUA was administered in two ways, i.e., intravenous administration and peroral administration at predetermined times. Nine weeks after, the area of the tumor of each mouse was measued and the inhibition rate (%) was calculated.
(3) Test results:
The test results are shown in Table 5-1.

TABLE 5-1

| Method of administration | Time of administration (weeks after) (the birth) | Dose (mg/kg) | Area of tumor (mm² ± S.E.) | Inhibition rate (%) |
|---|---|---|---|---|
| | | Control | $1.45 \pm 0.30$ | |
| iv | 5.6 | $40 \times 2$ | $0.75 \pm 0.22^X$ | 49.2 |
| | 5.7 | $40 \times 2$ | $0.79 \pm 0.31^X$ | 46.5 |
| | 5 | $40 \times 1$ | $0.91 \pm 0.81^{XX}$ | 37.2 |
| | | Control | $1.41 \pm 0.44$ | |
| po | 5,6,7,8 | $133 \times 4$ | $0.78 \pm 0.22^X$ | 44.7 |
| | | $200 \times 4$ | $0.78 \pm 0.16^X$ | 44.7 |
| | | $267 \times 4$ | $0.55 \pm 0.18^X$ | 61.0 |
| | | $333 \times 4$ | $0.66 \pm 0.14^X$ | 53.2 |

$^X p < 0.01$
$^{XX} p < 0.05$

In the above tests, it was recognized that CNUA (compound of the present invention) exhibit powerful antitumor effects on leukemia L-1210, P 388, Lewis lung carcinoma, β-16 melanoma and mouse lung autotumor to prolong the life of warm-blooded animals with such tumors or to inhibit the proliferation of the tumor cells in these warm-blooded animals.

Toxicity tests:

CNUA dissolved in isotonic sodium chloride solution was given to DDY male mice each weighing 20 to 22.5 g by intraperitoneal administration, intravenous administration and peroral administration, and $LD_{50}$ values were determined.

The test results are shown in Table 5-2.

TABLE 5-2

| Method of administration | $LD_{50}$ (mg/kg) |
|---|---|
| ip | 65.5 |
| iv | 80 |
| po | 550 |

Test Example 6

Comparison of effects of CNUA and Me-CCNU* on peripheral leukocyte count:

*Me-CCNU=1-(2-chloroethyl)-3-(trans-4-methylcyclohexyl)-1-nitrosourea.

(1) Test animals:

Six-week old DDY mice each weighing 22±1 g; one group comprising 5 male mice.

(2) Test method:

CNUA and Me-CCNU were given intraperitoneally on the first day. The blood was drawn from a tail vein at time intervals to determine the leukocyte count. The results are shown in Table 6. The samples were used in the form of a solution in an isotonic sodium chloride solution.

TABLE 6

| Compound tested | mg/kg | Peripheral leukecyte count after the administration (% based on the control) | | | | |
|---|---|---|---|---|---|---|
| | | 2 day | 4 day | 7 day | 10 day | 14 day |
| CNUA | 30 | 84.0 | 82.2 | 85.6 | 84.7 | 159 |
| | 60 | 78.2 | 60.0 | 64.5 | 80.0 | 100 |
| Me—CCNU | 20 | 55.0 | 53.3 | 50.2 | 59.5 | 145 |
| | 40 | 56.0 | 36.5 | 34.0 | 40.7 | 78.1 |

The above results suggest that, as compared with Me-CCNU, CNUA has a relatively low myelotoxicity.

What is claimed is:

1. New D-allose derivatives of formula (I):

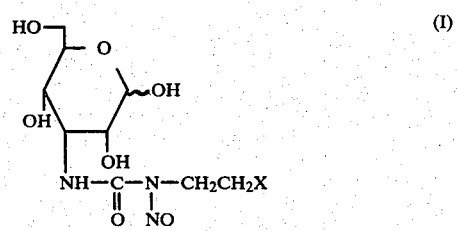

wherein X represents a halogen atom.

2. D-Allose derivatives according to claim 1 wherein X is chlorine.

3. An antitumor agent containing a compound of formula (I):

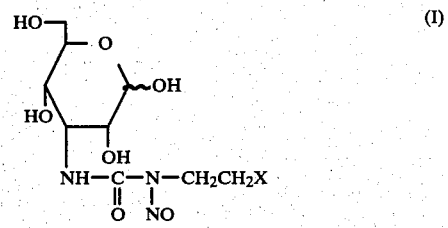

wherein X represents a halogen atom as active ingredient.

4. An antitumor agent according to claim 3 wherein X is chlorine.

* * * * *